United States Patent [19]

Monnier et al.

[11] Patent Number: 4,722,983
[45] Date of Patent: Feb. 2, 1988

[54] PROCESS FOR THE PREPARATION OF GLYCIDYL COMPOUNDS

[75] Inventors: Charles E. Monnier, Villars-sur-Glâne; Friedrich Stockinger, Courtepin, both of Switzerland

[73] Assignee: Ciba-Geigy Corporation, Ardsley, N.Y.

[21] Appl. No.: 939,213

[22] Filed: Dec. 8, 1986

[30] Foreign Application Priority Data

Dec. 13, 1985 [CH] Switzerland .......................... 5316/85

[51] Int. Cl.$^4$ ..................... C08G 59/06; C07D 301/27
[52] U.S. Cl. ................................... 525/507; 528/88; 528/89; 528/90; 528/93; 528/95; 549/517
[58] Field of Search ................. 549/516, 517; 528/88, 528/89, 90, 93, 95; 525/507

[56] References Cited

U.S. PATENT DOCUMENTS

| | | | |
|---|---|---|---|
| 4,269,952 | 5/1981 | Locatelli | 525/507 |
| 4,273,915 | 6/1981 | Soula et al. | 528/93 |
| 4,383,118 | 5/1983 | Locatelli et al. | 549/517 |
| 4,518,762 | 5/1985 | Krueger et al. | 525/507 |
| 4,582,892 | 4/1986 | Chang et al. | 528/93 |
| 4,634,713 | 1/1987 | Werner et al. | 514/392 |

FOREIGN PATENT DOCUMENTS

| | | |
|---|---|---|
| 60-31517 | 2/1985 | Japan . |
| 1485345 | 9/1977 | United Kingdom . |
| 2120659 | 12/1983 | United Kingdom . |

OTHER PUBLICATIONS

Chem. Abstr. 55, 14982.
Chem. Abstr. vol. 97, (1982) 217332x.
JACS, 101, 3666 (1979).
Chem. Abstr., vol. 78, 17230h (1973).
Makromol. Chem., 179, 1061 (1978).

Primary Examiner—Earl Nielsen
Attorney, Agent, or Firm—Luther A. R. Hall

[57] ABSTRACT

A process for the preparation of glycidyl compounds by reacting a compound containing at least one phenolic group with at least the equivalent amount, based on the phenolic group, of a halohydrin in a substantially anhydrous, aprotonic solvent in the presence of a solid, substantially anhydrous catalyst, is described, which process comprises carrying out the reaction at a temperature in the range from 40° to 80° C. in the presence of an alkali metal carbonate, an aprotonic dipolar solvent with a static relative dielectric constant of more than 25 (at 25° C.) and a permanent electric dipole moment of more than 2.5 D being used, an additional feature of said solvent being that the transition energy of the solvatochromic absorption band of the dissolved N-(3,5-diphenyl-4-hydroxyphenyl)-2,4,6-triphenylpyridinium perchlorate is in the range from 168 to 197.4 kJ/mole (at 25° C.), or which process comprises carrying out the reaction at a temperature in the range from 60° to 80° C. in the presence of an alkali metal hydroxide and a phase transfer catalyst chosen from the group consisting of ammonium and/or phosphonium compounds, the water of reaction formed being removed continuously and an inert, aprotonic, apolar solvent with a static relative dielectric constant of less than 8.0 (at 25° C.) and a permanent electric dipole moment of less than 2.0 D being used, an additional feature of said solvent being that the transition energy of the solvatochromic absorption band of the dissolved N-(3,5-diphenyl-4-hydroxyphenyl)-2,4,6-triphenylpyridinium perchlorate is in the range from 140 to 165 kJ/mole (at 25° C.).

The resins obtained in this manner have a high degree of epoxidation and a low content of hydrolysable or ionic halogen. They are particularly suitable as potting resins for electronic components.

14 Claims, No Drawings

PROCESS FOR THE PREPARATION OF GLYCIDYL COMPOUNDS

The present invention relates to an improved process for the preparation of glycidyl compounds and to the use of these products in the fields of surface protection, electrical engineering and electronics, laminating processes and construction.

Epoxy resins have long been used in the electronics industry. In recent years, the requirements made of these resins with regard to purity have increased continuously. In particular, small amounts of ionic or hydrolysable halogen can have a troublesome effect. Resins with the maximum possible degree of epoxidation are also increasingly in demand. As a rule, epoxy resins are prepared by reacting compounds containing reactive hydrogen atoms, preferably phenols, with epichlorohydrin. The reaction is generally carried out in an aqueous medium using a basic compound, preferably aqueous sodium hydroxide solution.

Proposals have been made to carry out the glycidylation reaction in organic solvents. However, aqueous alkali metal hydroxide is frequently used here, as a result of which the reaction does not take place under anhydrous conditions, or the phenol is used in the form of its alkali metal salt, thus making an additional process stage necessary. Examples of such reaction procedures are described in German Auslegeschrift No. 1,081,666 (reaction of the alkali metal salt of a phenol with halohydrin under anhydrous conditions in an organic solvent, for example an alcohol or ketone) or in Japanese published patent application No. 60-31,517 or East German patent specification No. 153,883 (reaction of a polyphenol with epichlorohydrin in aprotonic polar solvents in the presence of aqueous sodium hydroxide solution).

A two-stage process for the preparation of glycidyl compounds, which process comprises first reacting a polyphenol with epichlorohydrin in the presence of an alkylenephosphorane and then bringing the reaction to completion by the addition of, inter alia, solid alkali metal hydroxide, is also known from German Offenlegungsschrift No. 2,533,505.

Furthermore, U.S. Pat. No. 4,518,762 describes an improved process for the preparation of glycidyl ethers of novolak resins, which process comprises reacting the reactants in the presence of a small amount of water and in an alcohol as the solvent. The basic compound used is a solid alkali metal hydroxide, which is added in portions in the course of the reaction. The use of potassium carbonate in glycidylation reaction is described by D. E. McClure et al. in JACS 101, 3666 (1979). Acetone or dichloromethane is used as the solvent in the reaction.

A process for advancing glycidyl compounds, which process comprises reacting low molecular weight epoxide compounds with divalent phenols in an inert solvent, is known from German Offenlegungsschrift No. 2,205,097. Alkali metal hydroxides, quaternary ammonium or phosphonium salts or tertiary phosphines are required as catalysts. The solvents proposed are, in particular, chlorinated hydrocarbons, ketones or diethylene glycol (ethers). The reaction temperature in this process is in the range from 100° to 195° C.

Finally, a process in which a phenol is reacted with an excess of epichlorohydrin in an acetone/hexane mixture as solvent, in the presence of powdered potassium carbonate, is described in Embodiment Example 2 of published European patent application 96,006. The reaction is carried out under an inert gas at the boiling point of the reaction mixture. The reaction time is 74 hours.

A process has now been found in which the glycidylation reaction (cf. scheme) proceeds rapidly under very mild conditions and affords high yields. Products with a low content of hydrolysable and ionic halogen and a high content of epoxide groups are thereby formed.

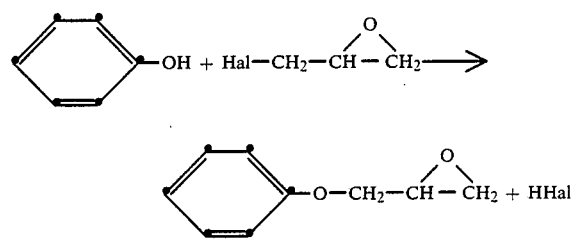

The present invention relates to a process for the preparation of glycidyl compounds by reaction of a compound containing at least one phenolic group with at least the equivalent amount, based on the phenolic group, of a halohydrin in a substantially anhydrous, aprotic solvent in the presence of a solid, substantially anhydrous, basic compound, which process comprises (a) carrying out the reaction at a temperature in the range from 40° to 80° C. in the presence of an alkali metal carbonate, an aprotonic dipolar solvent with a static relative dielectric constant of more than 25 (at 25° C.) and a permanent electric dipole moment of more than 2.5 D being used, an additional feature of said solvent being that the transition energy of the solvatochromic absorption band of the dissolved N-(3,5-diphenyl-4-hydroxyphenyl)-2,4,6-triphenylpyridinium perchlorate is in the range from 168 to 197.4 kJ/mole (at 25° C.), or (b) carrying out the reaction at a temperature in the range from 60° to 80° C. in the presence of an alkali metal hlydroxide and a phase transfer catalyst chosen from the group consisting of ammonium and/or phosphonium compounds, the water of reaction formed being removed continuously and an inert, aprotonic, apolar solvent with a static relative dielectric constant of less than 8.0 (at 25° C.) and a permanent electric dipole moment of less than 2.0 D being used, an additional feature of said solvent being that the transition energy of the solvatochromic absorption band of the dissolved N-(3,5-diphenyl-4-hydroxyphenyl)-2,4,6-triphenylpyridinium perchlorate is in the range from 140 to 165 kJ/mole (at 25° C.).

Compounds with at least one phenolic hydroxyl group which can be employed within the scope of this invention include substances with one or more phenolic nuclei, which nuclei may carry several hydroxyl groups, but prferably carry one hydroxyl group. The phenol nuclei may be unsubstituted or also contain additional substituents, for example one to four halogen atoms, preferably chlorine or bromine atoms, alkyl groups, preferably methyl, alkenyl groups, preferably ethenyl or allyl, or phenyl or benzyl groups.

Examples of phenolic components which are preferably used are phenol, o-, m- or p-cresol, 2-allylphenol, 2,6-diallylphenol, 2,4,6-triallylphenol, bis(hydroxyphenol)methane (bisphenol F; isomer mixture of o,o'-, o,p'- and p,p'-compounds), 1,1-bis(4-hydroxyphenyl)ethane, 2,2-bis(4-hydroxyphenol)propane (bisphenol A), tetrabromobisphenol A, tetrachlorobisphenol A, 1,1-bis(4-hydroxyphenyl)-1-phenylethane, 1,1'2,2'-tetrakis(4-hydroxyphenyl)ethane, resorcinol, hydroquinone or polyphenols which are derived from condensation of mononuclear phenols with aldehydes or ketones, in particular with formaldehyde (novolaks). Examples of these are phenol novolaks, o-cresol novolaks, p-cresol novolaks or resorcinol novolaks. Phenolic components which it is particularly preferred to use are bisphenol A, tetrabromobisphenol A, phenol novolaks or cresol novolaks, in particular o-cresol novolaks. Mixtures of these compounds can also be used. The novolaks employed preferably have molecular weights in the range from 300 to 1,000 (numerical average), most preferably molecular weights in the range from 400 to 700.

Examples of suitable halohydrins are epichlorohydrin, β-methylepichlorohydrin, epibromohydrin, β-methylepibromohydrin, glycerol dichlorohydrin or mixtures of these compounds. Epichlorohydrin is preferably used.

The choice of a suitable solvent plays an essential role when carrying out the process of the invention. Not every aprotonic, dipolar or aprotonic, apolar solvent is suitable for allowing the reaction to proceed at the desired rate. Furthermore, the terms "aprotonic, dipolar and aprotonic, apolar solvent" are not clearly defined (cf. Chr. Reichardt in "Lösungsmittel-Effekte in der organischen Chemie" (Solvent Effects in Organic Chemistry); Chapter 3.4; Verlag Chemie, 1973).

One possibility of characterising the polarity of a solvent consists in determining the transition energy of the solvatochromic absorption band of a dissolved pyridinium-N-phenolbetaine. This method is described by K. Dimroth et al. in Annalen der Chemie 661, 1 (1963).

Examples of aprotonic, dipolar solvents are 4-methyl-1,3-dioxol-2-one (propylene carbonate), acetonitrile, dimethyl sulfoxide, tetramethylenesulfone (sulfolane), dimethylformamide, dimethylacetamide, 1-methyl-2-pyrrolidone, nitrobenzene and hexamethylphosphoric acid triamide.

Aprotonic, dipolar solvents, as defined above, with a static relative dielectric constant of more than 30 are particularly preferred. Examples of such solvents are 4-methyl-1,3-dioxol-2-one, acetonitrile, dimethyl sulfoxide, tetramethylenesulfone, dimethylformamide, dimethylacetamide and 1-methyl-2-pyrrolidone.

Dimethyl sulfoxide and/or dimethylformamide are preferably used, dimethyl sulfoxide being particularly preferred. However, it is also possible to use solvent mixtures if they fall under the definition given above.

Examples of inert aprotonic, apolar solvents are chloroform, triethylene glycol dimethyl ether, ethylene glycol dimethyl ether, chlorobenzene, diethylene glycol diethyl ether, tetrahydrofuran, anisole, phenetole, 1,4-dioxane, diphenyl ether, diethyl ether, benzene, diisopropyl ether, toluene, ethylbenzene, xylene, mesitylene or di-n-butyl ether.

Particularly preferred inert, aprotonic solvents are tetrahydrofuran, 1,4-dioxane or toluene, most preferably toluene.

The solvent must be substantially anhydrous; the water content of the solvent employed is preferably less than 1% by weight, most preferably less than 0.5% by weight.

The basic compound in the process of the invention must also be substantially anhydrous and in solid form. It can be granular or in powdered form. A powdered substance is preferably used.

The entire amount of the basic compound can be dissolved in the solvent at the start of the reaction or can be present partly in suspended form. However, the basic compound can also be added in portions or continuously during the reaction.

The alkali metal hydroxide used is preferably lithium hydroxide or, in particular, sodium hydroxide or potassium hydroxide. It is particularly preferred to employ sodium hydroxide and potassium hydroxide, most preferably potassium hydroxide.

The alkali metal carbonate used is, for example, sodium carbonate, potassium carbonate or caesium carbonate. It is particularly preferred to employ potassium carbonate or caesium carbonate, most preferably potassium carbonate.

Mixtures of the individual basic compounds can also be used if these fall under the definition of the particular process variant. If appropriate, the process of the invention can be carried out under an inert gas, for example nitrogen or argon.

Particularly suitable phase transfer catalysts are quaternary ammonium or phosphonium salts, especially tetraalkylammonium or tetraalkylphosphonium compounds. A survey of possible phase transfer catalysts is given in the article by E. V. Dehmlow in "Angew. Chem., 89, 529 (1977)". Particularly preferred phase transfer catalysts are cetylammonium chloride or bromide, tetrakis(n-butyl)ammonium chloride, bromide or hydrogen sulfate, and tetrakisbutylphosphonium chloride, bromide or hydrogen sulfate.

The reaction time depends on the reactivity of the starting products employed, on the choice of the particular solvent, on the reaction temperature and on the nature and state of the basic compound. The reaction time is generally between 2 and 20 hours.

If an alkali metal carbonate is used as the basic compound, the reaction temperature is preferably chosen in the range from 40° to 60° C. or from 60° to 80° C., depending on whether a product with a particularly low content of hydrolysable halogen or with a particularly high degree of epoxidation is to be obtained. Products which are distinguished by a particularly low content of hydrolysable halogen are generally obtained at low temperatures, while a product with a higher degree of epoxidation is obtained at higher temperatures.

The halohydrin is preferably employed in an amount of 1.0–20.0 moles, based on one phenolic group of the phenolic component. It is particularly preferred for the halohydrin to be present in amounts of 1.5–10.0, most preferably 3.0–10.0, moles per phenolic hydroxyl group. The amount of basic compound is preferably chosen so that 1.0–10.0, preferably 1.0–5.0 and most preferably 1.0–3.0, equivalents of hydroxyl or carbonate anions are present per equivalent of phenolic hydroxyl group. The preferred amount of solvent is 1.0 to 20.0 moles, preferably 3.0 to 10.0 moles, per equivalent of phenolic group.

In a preferred embodiment of the process, the compound containing at least one phenolic hydroxyl group is charged with the powdered, anhydrous potassium carbonate into the anhydrous aprotonic, dipolar solvent, the solution or suspension is heated to 40°–80° C. and the halohydrin is added to the reaction mixture, with stirring. The rate of addition is adjusted so that the reaction temperature does not exceed 80° C. If necessary, the mixture can subsequently be allowed to after-react further in the temperature range from 40° to 80° C. The particular reaction time required can be monitored with the aid of the epoxide content of the reaction mixture. The molar ratio of phenolic component, halohydrin and solvent in this embodiment is between 1.3:3 and 1:5:5. 1.0–3.0 moles of basic compound are added per equivalent of phenolic group.

For working up, the solid consituents are separated off from the reaction mixture, for example by filtration. The residue is then concentrated and taken up in a water-immiscible organic solvent, for example in methyl ethyl ketone or methyl isobutyl ketone, in aromatic hydrocarbons such as benzene, toluene or xylene, or also in aliphatic hydrocarbons such as hexane, heptane or octane. This solution is then washed with water until the content of ionic impurities no longer decreases. It is then dried, for example over $Na_2SO_4$, and the solvent is removed.

If phenol or cresol novolaks are employed as starting materials in the process of the invention, it is to be regarded as particularly advantageous that no essential shift in the molecular weight distribution results in the glycidylated end products. In previously known glycidylation processes, the average molecular weight is as a rule increased. This results in an increased viscosity of the end products.

The novolak glycidylation products obtainable by the process of the invention are distinguished by a surprisingly low viscosity.

The resins obtained by the process of the invention are particularly suitable for use in the fields of surface protection, electrical engineering and electronics, laminating processes and construction. Low molecular types can be employed as reactive diluents.

The resins can be used in the particular formulation adapted to suit the specific intended use, in the non-filled or filled state, as components of compression moulding materials, dip-coating powders, casting resins, injection moulding formulations, impregnating resins, adhesives, tooling resins, laminating resins and powder coating formulations.

The novolak glycidylation products obtainable by the process of the invention are particularly suitable as potting resins for electronic components.

The invention also relates in particular to the use of the glycidylated phenol or cresol novolaks obtained by the above-defined processes as potting resins for electronic components.

EXAMPLES

General Procedure I 576 g (2 moles) of anhydrous powdered potassium carbonate or 2 moles of caesium carbonate and 462.5 g (5.0 moles) of epichlorohydrin are added to 1 equivalent of a compound containing a phenolic hydroxyl group in about 5 moles of an aprotonic, dipolar solvent in a 1.5 l sulfonating flask equipped with condenser, stirrer, thermometer and nitrogen inlet tube, and the mixture is reacted at 40°–80° C. for 4–20 hours. When the reaction has ended, the mixture is allowed to cool to room temperature and is filtered, and the filtrate is concentrated in vacuo in a rotary evaporator at 100°–130° C.

The residue is dissolved in methyl isobutyl ketone, the solution is washed twice with warm water, and the organic phase is dried over $Na_2SO_4$ and filtered, and the filtrate is concentrated.

The epoxide content of the crude product formed is between 70 and 97% of theory. The results are shown in the following table.

The molecular weights of the polymeric products are determined by means of gel permeation chromatography. The reaction conditions are listed in the following table.

| Example | Phenol Type | Aequivalents of OH | Moles of epichlorohydrin | Solvent Type | Solvent Moles | Base Type | Base Moles | Time [h] | Temperature [°C.] | Yield [%] | Epoxide content [equivalents Δ/kg] | $\overline{M}_n$ | $\overline{M}_w$ |
|---|---|---|---|---|---|---|---|---|---|---|---|---|---|
| 1 | 2,6-dimethylphenol | 1 | 5 | DMF | 5 | $K_2CO_3$ | 2 | 4 | 60 | 93 | 5.44 | | |
| 2 | 2,6-dimethylphenol | 1 | 5 | DMSO | 5 | $K_2CO_3$ | 2 | 5 | 60 | 93 | 5.44 | | |
| 3 | p-cresol | 1 | 5 | DMF | 5 | $K_2CO_3$ | 2 | 5 | 60 | 89 | 5.89 | | |
| 4 | polyphenol A (1) | 1 | 5 | DMF | 5 | $K_2CO_3$ | 2 | 5 | 60 | 89 | 4.80 | | |
| 5 | phenol novolak (3) | 1 | 5 | DMSO | 5 | $K_2CO_3$ | 2 | 5 | 80 | 90.3 | 5.92 | | |
| 6 | cresol novolak (2) | 1 | 5 | DMSO | 5 | $K_2CO_3$ | 2 | 20 | 40 | 93.1 | 5.14 | 920 | 1768 |
| 7 | cresol novolak (2) | 1 | 5 | DMSO | 5 | $K_2CO_3$ | 2 | 5 | 60 | 89.6 | 5.41 | 788 | 1414 |
| 8 | cresol novolak (2) | 1 | 5 | DMSO | 5 | $K_2CO_3$ | 2 | 5 | 80 | 96.5 | 5.21 | | |
| 9 | cresol novolak (2) | 1 | 3 | DMSO | 3 | $K_2CO_3$ | 2 | 5 | 80 | 87.9 | 5.24 | | |
| 10 | cresol novolak (2) | 1 | 5 | DMF | 5 | $K_2CO_3$ | 2 | 5 | 80 | 98.0 | 4.93 | | |
| 11 | cresol novolak (2) | 1 | 5 | DMSO | 5 | $K_2CO_3$ | 2 | 10 | 50 | 91.0 | 5.16 | 931 | 1613 |

(1) 1,1,2,2'-tetrakis(4-hydroxyphenyl)ethane
(2) $\overline{M}_n$:701 $\overline{M}_w$:945
(3) $\overline{M}_n$:401 $\overline{M}_w$:518

| Example | Phenol Type | Equivalents of OH | Moles of epichlorohydrin | Solvent Type | Solvent Moles | Base Type | Base Moles |
|---|---|---|---|---|---|---|---|
| 12 | cresol novolak (1) | 1 | 5 | DMSO | 5 | $K_2CO_3$ | 2 |
| 13 | cresol novolak (1) | 1 | 5 | $CH_3$—CN | 5 | $K_2CO_3$ (3) | 2 |
| 14 | cresol novolak (1) | 1 | 5 | DMSO | 5 | $K_2CO_3$ (3) | 2 |
| 15 | cresol novolak (1) | 1 | 5 | DMSO | 5 | $K_2CO_3$ (3) | 2 |
| 16 | cresol novolak (1) | 1 | 5 | $CH_3$—CN | 5 | $K_2CO_3$ | 2 |
| 17 | cresol novolak (1) | 1 | 5 | sulfolane | 5 | $K_2CO_3$ | 2 |

-continued

| | | | | | | | |
|---|---|---|---|---|---|---|---|
| 18 | cresol novolak (1) | 1 | 5 | propylene-carbonate | 5 | K₂CO₃ | 2 |
| 19 | phenol | 1 | 5 | DMSO | 5 | Cs₂CO₃ | 2 |
| 20 | 2,2-bis(4-hydroxyphenyl)-propane | 1 | 5 | DMSO | 5 | K₂CO₃ | 2 |

| Example | time [h] | Temperature [°] | Yield [%] | Epoxide content [equivalents Δ/kg] | Molecular weight $\overline{M}_n$ | Molecular weight $\overline{M}_w$ | Chlorine content (4) [ppm] |
|---|---|---|---|---|---|---|---|
| 12 | 20 | 40 | 93 | 5.14 | 920 | 1768 | 213 |
| 13 | 5 | 60 | 99 | 4.34 (2) | | | |
| 14 | 10 | 40 | 100 | 5.04 | 993 | 2042 | 662 |
| 15 | 10 | 50 | 98 | 5.16 | 931 | 1613 | 730 |
| 16 | 5 | 60 | 95 | 3.84 (2) | | | |
| 17 | 5 | 60 | 84 | 4.71 | 1025 | | |
| 18 | 5 | 60 | 95 | 3.75 (2) | | 2052 | 2500 |
| 19 | 5 | 60 | 92 | 6.19 | | | |
| 20 | 5.7 | 60 | 87.7 | 5.64 (5) | | | |

(1) $\overline{M}_n$: 701 $\overline{M}_w$: 945
(2) working up only as far as concentration by rotary evaporator
(3) additional with 2 mol % of tetrabutylammonium hydrogen sulfate (based on entire mixture)
(4) hydrolysable chlorine
(5) after working up with methyl isobutyl ketone (yield: 95.6%), a product with an epoxide content of 5.73 equiv. Δ/kg is obtained.

General Procedure II 1 equivalent of a compound containing a phenolic hydroxyl group in about 5 moles of an aprotonic, apolar solvent are charged together with 6 equivalent of epichlorohydrin and 2 mol % of tetrabutylammonium hydrogen sulfate into a 1.5 l sulfonating flask equipped with condenser, stirrer, thermometer and nitrogen inlet tube. The reaction mixture is warmed to 60°–80° C. and solid powdered alkali metal hydroxide is added, with simultaneous distillation of the water of reaction which forms. The reaction time is about 4 hours. When the reaction has ended, the reaction mixture is washed out with water. The results are shown in the following table.

| Example No. | Phenol | Solvent | Temperature (°C.) | Catalyst type + amount (moles) | Yield (% of theory) | Epoxide content (equivalents/kg) |
|---|---|---|---|---|---|---|
| 21 | cresol (1) novolak | toluene | 60 | KOH (2) | 95 | 5.32 (2) |
| 22 | cresol (1) novolak | toluene | 62–72 | NaOH (2) | 80 | 5.04 (3) |

(1) $\overline{M}_n$: 701 $\overline{M}_w$: 945
(2) $\overline{M}_n$: 831 $\overline{M}_w$: 1766
(3) $\overline{M}_n$: 824 $\overline{M}_w$: 1736

What is claimed is:

1. A process for the preparation of a glycidyl compound by reacting a compound containing at least one phenolic group with at least the equivalent amount, based on the phenolic group, of a halohydrin in a substantially anhydrous, aprotic solvent in the presence of a solid, substantially anhydrous, basic compound, which process comprises (a) carrying out the reaction at a temperature in the range from 40° to 80° C. in the presence of an alkali metal carbonate, an aprotonic dipolar solvent with a static relative dielectric constant of more than 25 (at 25° C.) and a permanent electric dipole moment of more than 2.5 D being used, an additional feature of said solvent being that the transition energy of the solvatochromic absorption band of the dissolved N-(3,5-diphenyl-4-hydroxyphenyl)-2,4,6-triphenylpyridinium perchlorate is in the range from 168 to 197.4 kJ/mole (at 25° C.), or (b) carrying out the reaction at a temperature in the range from 60° to 80° C. in the presence of an alkali metal hydroxide and a phase transfer catalyst chosen from the group consisting of ammonium and/or phosphonium compounds, the water of reaction formed being removed continuously and an inert, aprotonic, apolar solvent with a static relative dielectric constant of less than 8.0 (at 25° C.) and a permanent electric dipole moment of less than 2.0 D being used, an additional feature of said solvent being that the transition energy of the solvatochromic absorption band of the dissolved N-(3,5-diphenyl-4-hydroxyphenyl)-2,4,6-triphenylpyridinium perchlorate is in the range from 140 to 165 kJ/mole (at 25° C.).

2. A process according to claim 1, wherein the compound containing at least one phenolic group is phenol, o-, m- or p-cresol, 2-allylphenol, 2,6-diallylphenol, 2,4,6-triallylphenol, bis(hydroxyphenyl)methane, 1,1-bis(4-hydroxyphenyl)ethane, 2,2-bis(4-hydroxyphenyl)propane, tetrabromobisphenol A, tetrachlorobisphenol A, 1,1-bis(4-hydroxyphenyl)-1-phenylethane, 1,1',2,2'-tetrakis(4-hydroxyphenyl)ethane, resorcinol, hydroquinone or a novolak.

3. A process according to claim 1, wherein the halohydrin is epichlorohydrin, β-methylepichlorohydrin, epibromohydrin, β-methylepibromohydrin or glycerol dichlorohydrin or a mixture of these compounds.

4. A process according to claim 3, wherein the halohydrin is epichlorohydrin.

5. A process according to claim 1, wherein the aprotonic, dipolar solvent is 4-methyl-1,3-dioxol-2-one, acetonitrile, dimethyl sulfoxide, tetramethylene sulfone, dimethylformamide, dimethylacetamide, 1-methyl-2-pyrrolidone, nitrobenzene or hexamethylphosphoric acid triamide.

6. A process according to claim 5, which comprises the use of dimethylsulfoxide and/or dimethylformamide.

7. A process according to claim 1, wherein the inert, aprotonic, apolar solvent is chloroform, triethylene glycol dimethyl ether, ethylene glycol dimethyl ether, chlorobenzene, diethlyene glycol diethyl ether, tetrahydrofuran, anisole, phenetole, 1,4-dioxane, diphenyl ether, diethyl ether, benzene, diisopropyl ether, toluene, ethylbenzene, xylene, mesitylene or di-n-butyl ether.

8. A process according to claim 7, which comprises the use of tetrahydrofuran, 1,4-dioxane or toluene.

9. A process according to claim 1, wherein the phase transfer catalyst is cetylammonium chloride or bromide, tetrakis(n-butyl)ammonium chloride, bromide or hydrogen sulfate or tetrakis(n-butyl)phosphonium chloride, bromide or hydrogen sulfate.

10. A process according to claim 1, wherein the solid, substantially anhydrous basic compound is sodium hydroxide, potassium hydroxide, potassium carbonate or caesium carbonate.

11. A process according to claim 10, which comprises the use of potassium hydroxide.

12. A process according to claim 10, which comprises the use of potassium carbonate.

13. A process according to claim 1, wherein the halohydrin is used in an amount of 1.0–20.0 moles, based on one phenolic group of the phenolic component.

14. A process according to claim 1, wherein the amount of basic compound is chosen so that 1.0–10.0 equivalents of hydroxyl or carbonate anions are present per equivalent of phenolic hydroxyl group.

* * * * *